United States Patent [19]

Gates et al.

[11] 3,954,437

[45] May 4, 1976

[54] HERBICIDAL COMPOSITION

[75] Inventors: Donald W. Gates, Monroe, La.; Eldon S. Ratcliffe, Cottage Grove, Minn.; David J. Prochaska, Seneca, S.C.

[73] Assignee: Minnesota Mining and Manufacturing Company, St. Paul, Minn.

[22] Filed: Dec. 16, 1974

[21] Appl. No.: 532,888

[52] U.S. Cl. .................................. 71/91; 71/103
[51] Int. Cl.$^2$ ............................ A01N 9/22
[58] Field of Search ......................... 71/103, 91

[56] References Cited
UNITED STATES PATENTS

| 3,639,474 | 2/1972 | Harrington et al. ............ 71/103 |
| 3,708,277 | 1/1973 | Zeidler et al. ............ 71/91 |

*Primary Examiner*—Lewis Gotts
*Assistant Examiner*—Catherine L. Mills
*Attorney, Agent, or Firm*—Alexander, Sell, Steldt & DeLaHunt

[57] ABSTRACT

A herbicidal mixture of 5-acetamido-2,4-dimethyltrifluoromethanesulfonanilide or a horticulturally acceptable salt thereof and 3-isopropyl-1H-2,1,3-benzothiadiazin-(4)3H-one 2,2-dioxide or a horticulturally acceptable salt thereof is effective at low rates of application, particularly against certain weed species such as hemp sesbania (coffeeweed).

4 Claims, No Drawings

HERBICIDAL COMPOSITION

This invention relates to synergistic herbicidal compositions comprising a mixture of previously known herbicidal agents. The invention also relates to a method for combating weeds comprising applying an effective amount of a composition containing the mixture to soil after the emergence of weed plants.

BACKGROUND OF THE INVENTION

5-Acetamido-2,4-dimethyltrifluoromethanesulfonanilide, which can also be referred to as N-[2,4-dimethyl-5-[[(trifluoromethyl)sulfonyl]amino]phenyl] acetamide, is a known useful herbicide (see, for example, U.S. Pat. No. 3,894,078). This compound, which has the structure

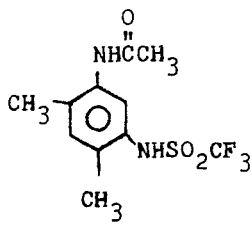

will be designated hereinafter as Compound A. The horticulturally acceptable salts thereof are also known useful herbicides.

The compound 3-isopropyl-1H-2,1,3-benzothiadiazin-(4)3H-one 2,2,-dioxide is also known to have utility as a herbicide (as described in U.S. Pat. No. 3,708,277). This compound, which has the structure

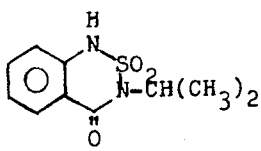

will be designated hereinafter as Compound B. The horticulturally acceptable salts of this compound are also known useful herbicides.

DETAILED DESCRIPTION OF THE INVENTION

This invention relates to compositions comprising mixtures of Compounds A and B, which have been found to be useful in combating both broadleaf and grass-like weeds. These compositions are particularly effective and synergistic in controlling hemp sesbania. Hemp sesbania or coffeeweed (*Sesbania exaltata*) is a broadleaf weed and its control in crops is of considerable economic significance.

More particularly the invention relates to herbicidal compositions comprising one part by weight of Compound A or a horticulturally acceptable salt thereof in admixture with from about 0.1 to 5 parts by weight of Compound B or a horticulturally acceptable salt thereof. Preferably the compositions contain from about 0.5 to 3 parts of Compound B (or its salt) to 1 part of Compound A (or its salt). Most preferably the compositions contain about one part of Compound B (or its salt) for each part of Compound A (or its salt). These combinations have synergistic herbicidal activity against the weed species while having little or no effect on the crop plants when suitably applied.

The invention also relates to a method for combating weeds by post-emergence application of these compositions.

The horticulturally acceptable salts of compounds A and B are prepared from the compounds themselves (the acid form compounds) by treating them with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by transmetallation reactions. The organic amine salts include the salts of alkylamines and aromatic amines, preferably containing not more than 10 carbon atoms. These and the ammonium salts can be prepared by reacting the acid form with the appropriate organic base or ammonium hydroxide. The salts of the invention are frequently formed by reacting the precursors in aqueous solution. This solution can be evaporated to obtain the salt of the compound as a dry powder. In some cases, it may be more convenient to use a nonaqueous solvent such as alcohols, acetone, etc. Since many of the salts are water soluble, they are often used in the form of aqueous solutions.

The formulations which are suitable for application are comprised of the compositions containing mixtures of both of the active ingredients and one or more herbicidal adjuvants and/or carriers and can be in either liquid or solid form. Specific formulations are useful to facilitate the application of the compounds at uniform rates and to achieve specific biological objectives such as controlling the availability of the herbicide, improving adherence to weed plants, distributing the agents uniformly through a top layer of the soil and the like, as is well known to those skilled in the art.

The combination of compounds of the invention may thus be formulated as wettable powders, emulsifiable concentrates, aqueous or nonaqueous solutions and/or suspensions, granules, dusts and the like. The compounds as such can be finely divided and dispersed or suspended in any of the usual aqueous media. Spreading agents, wetting agents, sticking agents or other adjuvants can be added as desired.

When emulsifiable concentrates are prepared, the active ingredients can be present in concentration of about 5% to 60% or more, depending upon solubility. The units of concentration are weight per unit weight. The active ingredients are soluble or dispersible in common organic solvents used in agriculture such as toluene, xylene, dichloromethane, chloroform, hexane and heptane or less highly refined aromatic or aliphatic hydrocarbons and mixtures thereof. Examples of these are coal tar fractions, straight run petroleum distillates, thermolytically or catalytically cracked hydrocabon oil, gas oil, light lubricating oil fractions, kerosene, mineral seal oil, and the like. In appropriate cases, oxygenated solvents such as ketones may be used in or as the carriers. These concentrates can be dispersed in water to permit the use of an aqueous spray. Admixture with a small amount of an orgaic surface active agent capable of lowering the surface tension of water is preferred, so as to produce more or less stable emulsions. Examples of surface active agents variously known as dispersing agents, wetting agents, or emulsifying agents comprise soft or hard soaps, morpholine or dimethylamine oleate, sulfonated fish, castor and petroleum oils, sodium salts of lignin sulfonic acid, alkylated aromatic sodium sulfonates, such as decylbenzene sodium sulfonate, dodecylbenzene sodium sulfonate, butyl or other amine salts of decyl or dodecylbenzene sulfonic acid, sodium lauryl sulfate, disodium monolauryl phosphate, ethylene oxide condensation products of alkyl phenols, as for example octyl phenol, ethylene oxide condensation products of tall oil and ethylene oxide condensation products of higher alcohols or higher mercaptans. Mixtures of two or more surface active agents are also feasible. Generally, the surface active agent will comprise only a small proportion of the composition, say 0.1–15% by weight of the toxicant.

The formulation of dry compositions for applications as granules, dusts or for further dilution with liquid carriers is readily accomplished by mixing the finely divided toxicants with a solid carrier. Such solid carriers will be of various sizes from dust to granules. The techniques for such formulations are well known to the art. Suitable carriers include charcoal, talc, clay pyrophyllite, silicas, fuller's earth, lime diatomaceous earth, flours such as walnut shell, wheat, soya bean, cottonseed, and wood flours, magnesium and calcium carbonate, calcium phosphate and the like. Powders may be granulated by the use of suitable binders such as cellulose derivatives, for example ethyl or carboxymethyl cellulose corn syrup, and the like. The compounds of the above formulations are applied by spraying, spreading, dusting or the like. Local conditions, for example temperature, humidity, moisture content of the soil, nature of the soil, and the like, have an affect on the optimum rate of application, but the herbicidal combinations of the invention generally exhibit satisfactory control of broadleaf and grass weeds at the application rate of about 0.1 to 5 pounds per acre.

The herbicidal compositions of the invention may also contain other biologically active substances. Thus, insecticides and fungicides may be incorporated into the compositions. Further, if desired, the herbicidal compositions may contain fertilizers, trace metals or the like and, when applied directly to the soil, may additionally contain nematocides, soil conditioners, plant growth regulators, and/or herbicides of similar or different properties.

The following experimental field runs demonstrate the synergistic effects of the herbicidal combination of this invention against hemp sesbania.

An aqueous formulation of Compound A potassium salt was used. The sodium salt of Compound B was added in the proportions shown in Table I. All treatments contained 0.5% of an alkylarylpolyoxyethylene glycol surfactant. The mixtures were applied as a tank mix at three different locations in Louisiana. The chemicals were applied post-emergence at a rate of 25 gallons spray per acre on test plots having a moderate to heavy infestation of hemp sesbania.

Location 1 was Collinston, Louisiana. The chemicals were applied to areas containing hemp sesbania from about 1 to 10 inches high. The observations reported in the following table were made 47 days after application of the chemicals.

Location 2 was Mer Rouge, Louisiana. The chemicals were applied to areas containing hemp sesbania from about 2 to 5 feet high. The observations reported in the following table were made 21 days after application of the chemicals.

Location 3 was St. Joseph, Louisiana. The chemicals were applied to areas containing hemp sesbania from about 3 to 5 feet high. The observations reported in the following table were made 23 days after application of the chemicals.

The test results, recorded as percent kill compared to untreated controls, are summarized in the following table:

TABLE I

| APPLICATION RATE (LB./ACRE) | | CONTROL OF HEMP SESBANIA (PERCENT KILL) | | |
|---|---|---|---|---|
| CPD. A | CPD. B | LOCATION 1 | LOCATION 2 | LOCATION 3 |
| 0.25 | 0.00 | 60 | — | — |
| 0.50 | 0.00 | 67 | 57 | 53 |
| 1.00 | 0.00 | 80 | 63 | 57 |
| 1.50 | 0.00 | — | — | 63 |
| 0.00 | 0.50 | — | 7 | 23 |
| 0.00 | 1.00 | 33 | 23 | 30 |
| 0.00 | 1.50 | — | — | 53 |
| 0.50 | 0.50 | 95 | 93 | 95 |
| 0.50 | 1.00 | — | 80 | 95 |
| 0.50 | 1.50 | — | — | 100 |
| 1.00 | 0.50 | — | 88 | 97 |
| 1.00 | 1.00 | — | 92 | 97 |
| 1.00 | 1.50 | — | — | 100 |
| 0.00 | 0.00 | 0 | 0 | 0 |

What is claimed is:

1. A herbicidal composition characterized by containing, in effective amounts, an admixture of one part by weight of 5-acetamido-2,4-dimethyltrifluoromethanesulfonanalide or a horticulturally acceptable salt thereof with from about 0.1 to 5 parts by weight of 3-isopropyl-1H-2,1,3-benzothiadiazin-(4)3H-one 2,2-dioxide or a horticulturally acceptable salt thereof as active components.

2. A composition according to claim 1 dispersed in an agriculturally acceptable carrier.

3. A method for combating hemp sesbania which comprises applying to said hemp sesbania after its emergence from the soil an effective amount of a composition according to claim 1.

4. A method for combating the growth of hemp sesbania which comprises applying to said hemp sesbania after its emergence from the soil an effective amount of a dispersion according to claim 2.

* * * * *